US012268710B2

(12) United States Patent
Voelkel et al.

(10) Patent No.: US 12,268,710 B2
(45) Date of Patent: *Apr. 8, 2025

(54) METHOD OF TREATING SEVERE FORMS OF PULMONARY HYPERTENSION

(71) Applicant: ReversPAH LLC, Denver, CO (US)

(72) Inventors: Norbert F. Voelkel, Denver, CO (US); Charles Magolske, Denver, CO (US)

(73) Assignee: ReversPAH LLC, Denver, CO (US)

( * ) Notice: Subject to any disclaimer, the term of this patent is extended or adjusted under 35 U.S.C. 154(b) by 886 days.

This patent is subject to a terminal disclaimer.

(21) Appl. No.: 16/910,447

(22) Filed: Jun. 24, 2020

(65) Prior Publication Data

US 2020/0405748 A1 Dec. 31, 2020

Related U.S. Application Data

(60) Provisional application No. 62/866,781, filed on Jun. 26, 2019.

(51) Int. Cl.
*A61K 33/02* (2006.01)
*A61K 33/04* (2006.01)
*A61K 9/00* (2006.01)
*A61K 45/06* (2006.01)

(52) U.S. Cl.
CPC .............. *A61K 33/02* (2013.01); *A61K 33/04* (2013.01); *A61K 9/0019* (2013.01); *A61K 9/0053* (2013.01); *A61K 45/06* (2013.01)

(58) Field of Classification Search
CPC ...... A61K 33/02; A61K 33/04; A61K 9/0053; A61K 45/06; A61K 33/24; A61K 33/34; A61K 47/52; A61K 9/0019; A61P 9/12
See application file for complete search history.

(56) References Cited

U.S. PATENT DOCUMENTS

| | | | |
|---|---|---|---|
| 2007/0207191 A1* | 9/2007 | Kanzer | A61K 9/2846 424/643 |
| 2011/0287110 A1* | 11/2011 | Dewhirst | A61K 45/06 514/479 |
| 2017/0020828 A1* | 1/2017 | Devi | A61K 33/34 |
| 2020/0405748 A1 | 12/2020 | Voelkel et al. | |
| 2022/0040227 A1* | 2/2022 | Voelkel | A61K 45/06 |
| 2023/0226105 A1* | 7/2023 | Voelkel | A61K 31/723 424/617 |

FOREIGN PATENT DOCUMENTS

| | | |
|---|---|---|
| CN | 106257609 A | 12/2016 |
| WO | 03077901 A1 | 9/2003 |
| WO | WO-2012122295 A2 * | 9/2012 ............ A61K 31/155 |

OTHER PUBLICATIONS

By Sigma (Millipore Sigma product search 2024). (Year: 2024).*
Office Action issued on Sep. 28, 2022 in connection with corresponding Chinese Application No. 201910964866.7 (12 pp).
Harm J. Bogaard et al., "Copper Dependence of Angioproliferation in Pulmonary Arterial Hypertension in Rats and Humans" American Journal of Respiratory Cell and Molecular Biology, vol. 46, 2012, (pp. 582-591).
Aysar Al-Husseini et al., "Increased Eicosanoid Levels in the Sugen/Chronic Hypoxia Model of Severe Pulmonary Hypertension" Plos One, Mar. 18, 2015, (pp. 1-17).
Office Action issued on Sep. 28, 2022 in connection with corresponding Chinese Application No. 201910964866.7 (6 pp).
Aysar Al-Husseini et al., "Increased Eicosanoid Levels in the Sugen/Chronic Hypoxia Model of Severe Pulmonary Hypertension" Plos One, Mar. 18, 2015, (pp. 1-17).
Office Action issued on Feb. 24, 2023, in corresponding Chinese Application No. 201910964866.7, 12 pages.
International Search Report and Written Opinion issued on Jan. 14, 2022 in corresponding International PAtent Application No. PCT/US2021/047297; 16 pages.
Voelkel, et al., "A new treatment for severe pulmonary arterial hypertension based on an old idea: inhibition of 5-lipoxygenase", Pulmonary Circulation, 2020, pp. 1-8, vol. 10; 8 pages.
Xu, et al., "Chinese Herbal Medicine for Wilson's Disease: A Systematic Review and Meta-Analysis", Frontiers in Pharmacology, 2019, pp. 1-15, vol. 10; 15 pages.
Farkas, et al., "Nuclear Factor kB Inhibition Reduces Lung Vascular Lumen Obliteration in Severe Pulmonary Hypertension in Rats", American Journal of Respiratory Cell and Molecular Biology, 2014, pp. 413-425, vol. 51; 13 pages.
Ishida, et al., "Bioavailable copper modulates oxidative phosphorylation and growth of tumors", PNAS, 2013, p. 19507-19512, vol. 110; 6 pages.
Tuder, et al., "Exuberant Endothelial Cell Growth and Elements of Inflammation Are Present in Plexiform Lesions of Pulmonary Hypertension", American Journal of Pathology, 1994, pp. 275-285, vol. 144; 11 pages.
Humbert, et al., "Increased Interleukin-I and Interleukin-6 Serum Concentrations in Severe Primary Pulmonary Hypertension", American Journal of Respiratory and Critical Care Medicine, 1995, pp. 1628-1631, vol. 151; 4 pages.
Tian, et al., "Blocking Macrophage Leukotriene B4 Prevents Endothelial Injury and Reverses Pulmonary Hypertension", Sci Transl Med. Author manuscript, 2014, pp. 1-32; 32 pages.

(Continued)

*Primary Examiner* — Alma Pipic
(74) *Attorney, Agent, or Firm* — Maier & Maier, PLLC

(57) ABSTRACT

A method of treating severe forms of PH, including PAH, in a patient is provided. The method includes administering at least one copper chelator comprising a tetrathiomolybdate (TTM) salt. The method may further include administering at least one active agent that enhances treatment such as methotrexate, inhibitors of the 5-lipoxygenase enzyme (5-LO), rituximab, baicalin, inhibitors of immune checkpoints CTLA-4, PD-1 and PDL-1, bufalin, quercetin, curcumin, integrins, inhibitors of NF-kappaB, and focal adhesion kinase inhibitors. Also provided is a composition including the TTM salt and the at least one active agent.

13 Claims, 8 Drawing Sheets

(56) References Cited

OTHER PUBLICATIONS

Al-Husseini, et al., "Increased Eicosanoid Levels in the Sugen/Chronic Hypoxia Model of Severe Pulmonary Hypertension", Plos One, 2015, pp. 1-17; 17 pages.

Al-Husseini, et al., "Vascular endothelial growth factor receptor 3 signaling contributes to angioobliterative pulmonary hypertension", the Pulmonary Vascular Research Institute, 2015, pp. 101-116, vol. 5; 16 pages.

Cool, et al., "The hallmarks of severe pulmonary arterial hypertension: the cancer hypothesis—ten years later", The American Journal of Physiology-Lung Cellular and Molecular Physiology, 2020, pp. L1115-L1130; 16 pages.

Bogaard, et al., "Copper Dependence of Angioproliferation in Pulmonary Arterial Hypertension in Rats and Humans", American Journal of Respiratory Cell and Molecular Biology, 2012, pp. 582-591, vol. 46; 10 pages.

Kwapiszewska, et al., "The Role of the Aryl Hydrocarbon Receptor/ARNT/Cytochrome P450 System in Pulmonary Vascular Diseases—A Hypothesis", Circulation Research, 2019, pp. 1-22; 22 pages.

Mandinov, et al., "Copper chelation represses the vascular response to injury", PNAS, 2003, pp. 6700-6705, vol. 100; 6 pages.

Examination Report issued on Dec. 14, 2023, in corresponding United Kingdom Application No. 2219338.7, 2 pages.

Examination Report issued on May 13, 2024, in corresponding United Kingdom Application No. 2219338.7, 4 pages.

Examination Report issued on Feb. 23, 2024, in corresponding German Application No. 2219338.7, 6 pages.

Ribeiro, "Diethylcarbamazine: A potential treatment drug for pulmonary hypertension?", Toxicology and Applied Pharmacology, vol. 333, Aug. 26, 2017, pp. 92-99.

Examination Report issued on Oct. 3, 2024, in corresponding United Kingdom Application No. GB2219338.7, 6 pages.

\* cited by examiner diethylcarbamazine

| | |
|---|---|
| Molecular Formula | $C_{10}H_{21}N_3O$ |
| Average mass | 199.293 Da |
| Monoisotopic mass | 199.168457 Da |
| ChemSpider ID | 2944 |

METHOD OF TREATING SEVERE FORMS OF PULMONARY HYPERTENSION

CROSS-REFERENCE TO RELATED APPLICATIONS

The present patent application claims benefit and priority to U.S. Provisional Patent Application No. 62/866,781 entitled "METHOD OF TREATING SEVERE FORMS OF PULMONARY HYPERTENSION" filed on Jun. 26, 2019, which is hereby incorporated by reference into the present disclosure.

BACKGROUND

Over the last 30 years pulmonary arterial hypertension (PAH) research and therapy have been focused on pulmonary vasoconstriction and vasodilator treatment, and within the last 10 years researchers have developed the modern cell-based disease concepts.

It is now almost universally held that severe PAH develops in susceptible individuals—that may have a genetic predisposition—after injury to the lining cells of the small lung resistance vessels. These endothelial cells die (undergo apoptosis), and this cell death is then followed by exuberant, lumen-occluding cell growth. These lumen-occluding cells are abnormal in that they are apoptosis-resistant. There are several candidate proteins (growth factors and their receptors) that are likely involved in complex cell-cell interactions that have been summarized as "wound healing gone awry" (Voelkel et al. European Respiratory Journal, 2012 40: 1555-1565). The greater the number of occluded small resistance vessels, the higher the resistance to lung vessel blood flow. As this patho-biological concept is gaining wide acceptance, investigators are examining non-vasodilator treatment strategies. This invention aims to accomplish disease modification.

Lung vascular lesions in established PAH are complex, and there are many avenues that in different patients can lead to the development of pulmonary hypertension (PH). In addition to the idiopathic forms of PAH (IPAH), which include heritable PAH due a small number of known gene mutations, there is severe PAH associated with congenital heart defects, associated with interstitial lung diseases, collagen-vascular diseases, HIV/AIDS, schistosomiasis infection and chronic liver disease. In all of these forms of PH, and also the rare form of pulmonary veno-occlusive disease, the pathological changes of the lung vessels are severe. In addition to a genetic—or otherwise—predisposition a second factor or several additional factors re need for severe PAH to develop. This is illustrated by the fact that for any known PH risk factor there is only a small number of people that actually develop severe PH. These second factors can be drugs, cigarette smoke toxins (including heavy metals), viral infections, immune system abnormalities, including antibodies directed against the lungs and cell growth stimulated by hormones, one example being estrogen.

Moreover, as in many cancers, the lung tissue of rats subjected to protocols, which cause experimental PH, contains elevated levels of copper. There is one report stating that blood levels of copper are elevated in patients with "primary"—now called idiopathic PAH.

Prior to the present invention, however, the role of copper in lung vascular cell growth, vascular inflammation and angiogenesis in the context of PH and PAH was unknown, or at least not considered, in the treatment of PH and PAH.

SUMMARY

The present inventors have discovered that high levels of extracellular and intracellular copper play a critically important role in the pathogenesis of severe PH and PAH, and the present invention proposes modifying the influence of copper on lung vascular cell growth, vascular inflammation and angiogenesis by copper chelation. Specifically, some exemplary embodiments concern treating a patient suffering from severe PH and PAH by the administration of a therapeutically effective amount of a copper chelator comprising a tetrathiomolybdate $[(MoS_4)^{-2}]$ salt, hereinafter TTM salt.

The present inventors also discovered that the treatment of severe PH and PAH may be further enhanced by the combination of the copper chelator comprising the TTM salt and at least one active agent selected from methotrexate, inhibitors of the 5-lipoxygenase enzyme (5-LO), such as diethylcarbamazine and zileuton, rituximab, baicalin, inhibitors of immune checkpoints CTLA-4, PD-1 and PDL-1, such as NKTR 214 and NKTR 358, bufalin, quercetin, curcumin, integrin inhibitors, inhibitors of NF-kappaB, such as Apigenin and indole-3-carbinol, and focal adhesion kinase inhibitors such as disulfiram, fucoxanthinol, and nitandenib. The copper chelator comprising the TTM salt and at least one active agent may be administered separately. For example, the copper chelator comprising the TTM salt may be administered orally and the at least one active agent may be administered intravenously or orally.

The present invention also provides a composition comprising effective amounts of the copper chelator comprising a TTM salt and at least one active agent selected from methotrexate, inhibitors of the 5-lipoxygenase enzyme (5-LO), such as diethylcarbamazine and zileuton, rituximab, baicalin, inhibitors of immune checkpoints CTLA-4, PD-1 and PDL-1, such as NKTR 214 and 358, rituximab, bufalin, quercetin, curcumin, integrins, inhibitors of NF-kappaB, such as Apigenin and indole-3-carbinol, and focal adhesion kinase (FAK) inhibitors such as disulfiram, fucoxanthinol, and nintedanib, and pharmaceutically acceptable carriers and/or excipients. Such compositions may be in an intravenous form or an oral form, such as a tablet, a microtablet, or a capsule. The oral forms may provide a delayed release of the TTM salt after passage through the stomach.

BRIEF DESCRIPTION OF THE FIGURES

Advantages of embodiments of the present invention will be apparent from the following detailed description of the exemplary embodiments. The following detailed description should be considered in conjunction with the accompanying figures in which.

DETAILED DESCRIPTION

Aspects of the present invention are disclosed in the following description directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Copper, due to its Fenton Chemistry, serves as an important cofactor for numerous proteins and enzymes involved in both physiologic and pathological process. The proteins are secreted, intracellular or transmembraneous. There are more than 50 copper-binding proteins in the various compartments of a cell (membrane, cytoplasm, nucleus and mitochondria) they function as copper transporters, chaperones and enzymes. In theory all of these copper-binding proteins may be affected to various degrees by the copper chelator TTM.

The present invention is based on the discovery that high levels of extracellular and intracellular copper play a critically important role in the pathogenesis of severe PH and PAH.

The present inventors understood that disease modification of PH and PAH can only be accomplished if and when lung vessel lumen-obliterating cells are being removed.

Figure 1:
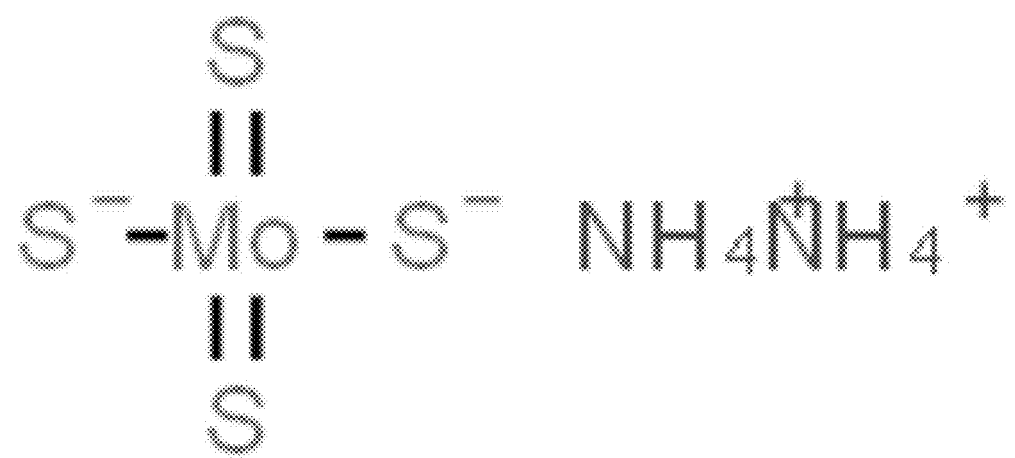
FIG. 1 shows the structure of an exemplary TTM salt of the present invention, specifically the ammonium salt of TTM, or ATTM.

In the Sugen 5416/chronic hypoxia rat model of severe PAH, which is characterized by small lung vessel occlusions by abnormally proliferating cells, it was discovered by Norbert F. Voelkel, that a copper-depleted diet prevented the development of PAH, and treatment of established severe PAH in these rats for two weeks with a copper chelator comprising an ammonium salt of tetrathiomolybdate $[(MoS_4)^{-2}]$ as shown in FIG. 1, also known as ATTM, which is a highly effective copper chelator, reversed the PAH. The effects of the copper chelator comprising this TTM salt included the reopening of occluded lung vessels and cut the pulmonary arterial pressure in half.

Moreover, experimental studies in rats by Norbert F. Voelkel have shown that there is a strong correlation between the pulmonary arterial or right ventricular systolic pressure and vascular obliteration. The more vessels are occluded, the higher the pressure.

It follows that re-opening of occluded small lung vessel would drastically decrease the elevated pulmonary artery pressure and thereby reduce the afterload of the right ventricle and thus the right heart stress. Patients with severe PAH and right heart failure display an elevation of the heart failure biomarker brain natriuretic protein (BNP). During treatment of PAH patients with copper chelator comprising the TTM salt, as the pulmonary artery pressure falls and the right ventricle function improves, there will be predicted a large decrease of the serum BNP level. Thus, a simple blood test can be serially performed to track the treatment effect of the copper chelator comprising the TTM salt. In addition, the dosing of the TTM will be individually adjusted to target a ceruloplasmin level of 50% of normal. This management of the ceruloplasmin level (1) protects against side effects from too much TTM and (2) validates we have provided effective dose of the TTM. The improvement of right heart function is documented with standard echocardiography and cardiac MRI studies.

The proposed mechanism of action of the copper chelator comprising the TTM salt in PAH patients is threefold: induction of anoikis of lumen-obliterating cells, reduction of vascular cell inflammation, and differentiation of stem cells in and around the pulmonary vascular lesions.

Figure 3:
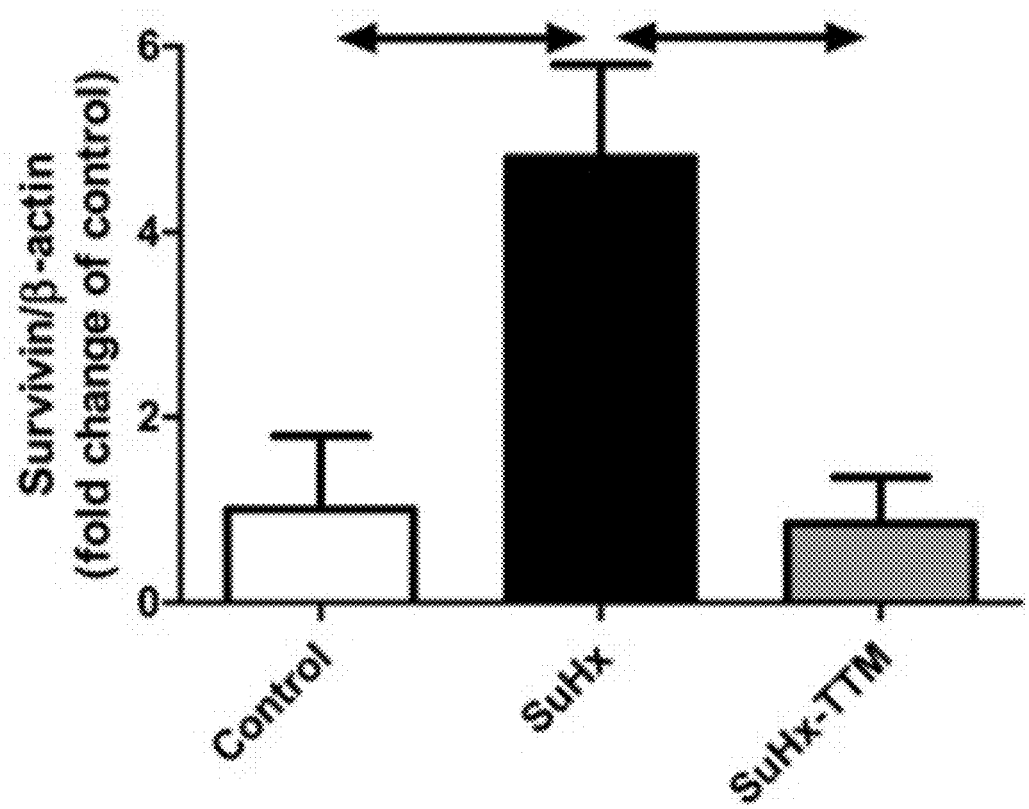
FIG. 3 compares the expression of the anoikis marker protein BIM in a normal control lung, a lung from Sugen/Hypoxia rats (SuHx) and a lung from SuHx rats treated with TTM (SuHx-TTM); the figure which was also previously published in Bogaard et al., Am J Respir Crit Care ed., 2012; 46: 582-591; the expression of this anoikis marker protein is referenced to the expression of a so-called house-keeping protein, in this case beta-actin.

From the studies based on the rat Sugen/hypoxia model of severe, lumen-obliterating pulmonary vascular disease, the present inventors concluded that the treatment strategy should focus on inducing anoikis, or cell death due to loss of cell adhesion to its matrix, in lumen-obliterating apoptosis-resistant cells, because one marker of anoikis, the protein BIM, was upregulated in the lung tissue by TTM treatment. FIG. 3, from the paper which included Norbert F. Voelkel as a senior author, shows the effect of TTM treatment on the expression of the anoikis marker BIM Beta-actin3 in a normal control rat lung, lungs from SuHx rats (SuHx), and lungs from a SuHx rats treated with TTM (SuHx-TTM).

In the context of PAH, it is desirable to induce anoikis of pulmonary vascular cells, which are abnormal endothelial cells, myofibroblasts and inflammatory cells. In the context of peripheral vascular disease and coronary artery disease, the induction of apoptosis of vessel lumen-obliterating cells is likewise desirable.

Anoikis can be induced by copper-chelating agents, such as by a TTM salt. Anoikis causes the phenotypically abnormal cells to die, and by reducing the number of abnormal cells, interrupts cell-cell communications that influence the growth and behavior of vascular stem cells and bone-marrow-derived progenitor cells, which are responsible for the persistence of the smoldering vessel inflammation and progressive vessel obliteration.

Thus, growth of cells inside the artery that occlude the artery are removed because the administered copper chelator comprising the TTM salt causes cells to lift off from other cells (i.e. anoikis) that are occluding the vessel lumen. As the number of abnormal cells occluding the vessel lumen is reduced, so is the strength of the signals emitted from the abnormal cells that attract inflammatory—and immune cells, resulting in a reduction of inflammation and in a modification of stem cell behavior. The modification of stem cell behavior is that stem cells stop dividing and become differentiated, i.e. the abnormal endothelial cells and smooth muscle cells become normal again. Then, as this happens, as the number of occluded vessels deceases, this drops the pulmonary artery pressure and subsequently improves right heart function.

Taken together, the three effects of anoikis, plus anti-angiogenesis, plus anti-inflammation and normalization of integrin receptor signaling and partial restoration of a normal extracellular matrix in concert, allow the reversal of PAH.

Figure 4:
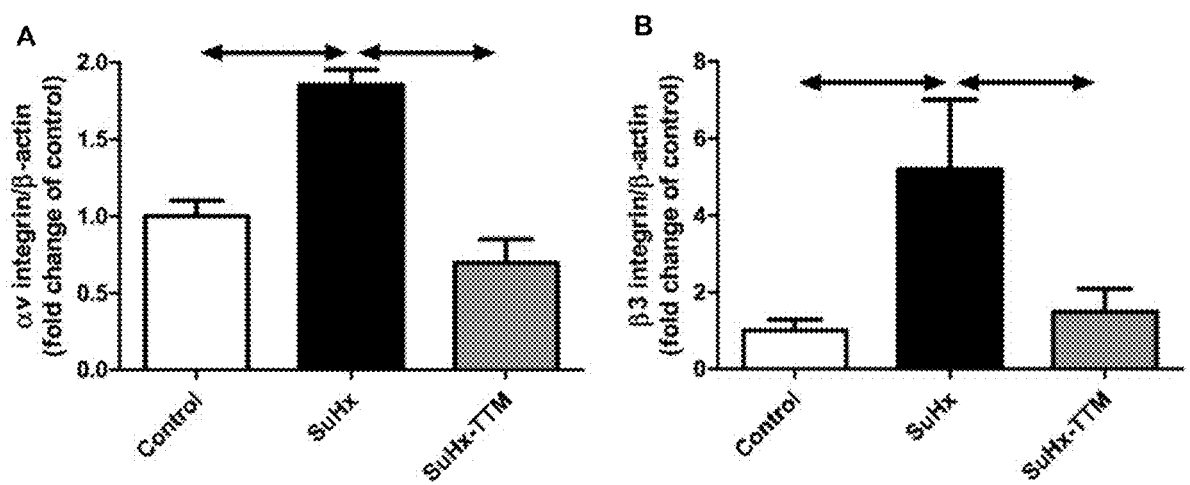
FIGS. 4A and B compare the expression of the integrin receptor alpha v and beta 3 in in a normal control rat lung, Sugen/Hypoxia rats (SuHx) with established PAH, and Sugen/Hypoxia rats (SuHx) treated with TTM (SuHx-TTM) in an amount of 10 mg/kg every other day for 10 days; these figures were also previously published in Bogaard et al., Am J Respir Crit Care Med., 2012; 46: 582-591.
Figure 5:
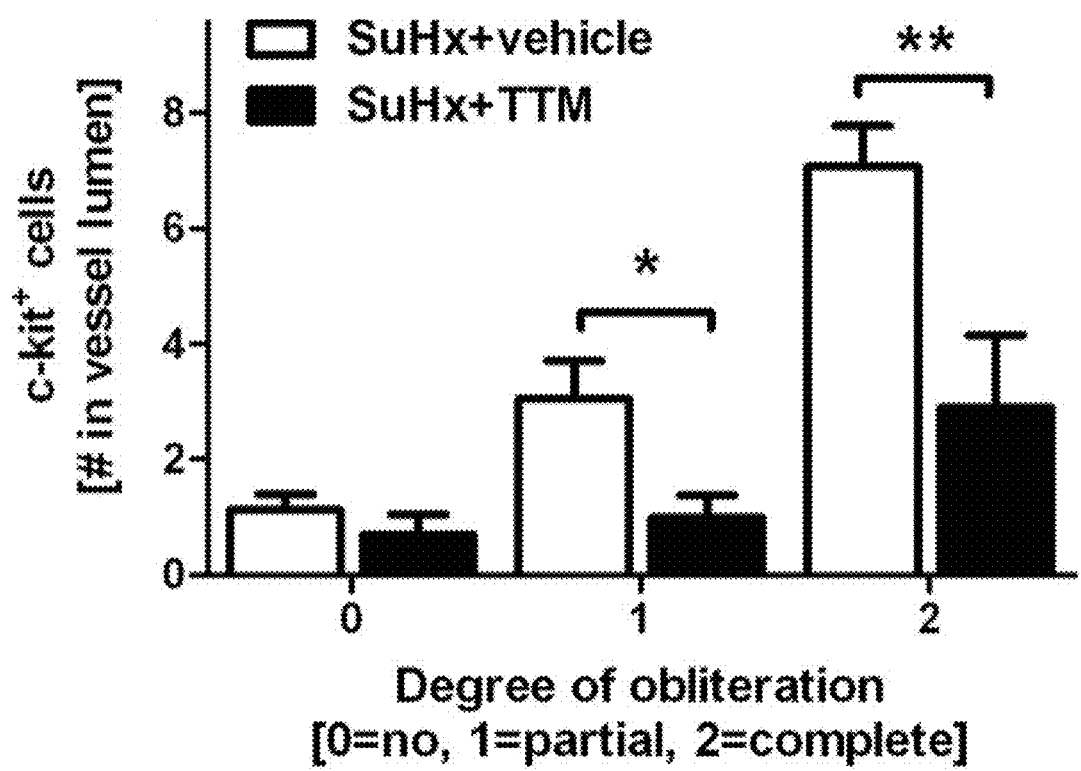
FIG. 5 compares the degree of obliteration of c-kit$^+$ expressing stem cells in the lung vessels of Sugen/Hypoxia rats (SuHx) treated with a vehicle (SuHx-vehicle) and Sugen/Hypoxia rats treated with TTM (SuHx-TTM) in an amount of 10 mg/kg every other day for 10 days, which was obtained from the rats studied and reported in Bogaard et al., Am J Respir Crit Care Med., 2012; 46: 582-591 (* designates the statistical significance level of $p<0.05$; ** designates a significance level of $p>0.01$)

The present inventors' work has shown the following: treatment with the copper chelator comprising a TTM salt induced anoikis as evidenced by cells expressing the anoikis-specific marker, for example the protein BIM; treatment with the copper chelator comprising a TTM salt also normalized the high expression of the integrin protein alpha v beta 3 in the TTM-treated lungs. Specifically, FIGS. 4A and B, which are from the paper which included Norbert F. Voelkel as a senior author, show the compared results of control rats, Sugen/Hypoxia rats (SuHx) with established PAH, and SuHx rats treated with TTM in an amount of 10 mg/kg every other day for 10 days. Treatment with the copper chelator comprising a TTM salt also reduced the number of c-kit+ precursor cells in the lung vascular lesions. FIG. 5 provides the results, which compares the degree of obliteration of c-kit$^+$ expressing stem cells in the lung vessels of Sugen/Hypoxia rats (SuHx) treated with a vehicle (SuHx-vehicle) and Sugen/Hypoxia rats treated with TTM (SuHx-TTM) in an amount of 10 mg/kg every other day for 10 days.

Based on these studies, it is hypothesized by the present inventors that treatment with the copper chelator comprising a TTM salt will induce anoikis only in the abnormal, lumen-occluding pulmonary vascular cells—but not in normal vessel wall cells. This reversal of lumen occlusion by a copper chelator comprising a TTM salt will lead to a drop of the high pulmonary vascular resistance (PVR) and to improvement of the right ventricular function of the right ventricle stressed by the high pulmonary artery pressure.

Also, the present inventors determined that copper levels influence lung vascular cell growth, vascular inflammation and angiogenesis. This discovery is based on the identification of five copper-dependent mechanisms.

First, copper is involved in stabilizing the ubiquitous transcription factor protein hypoxia-inducible factor 1-alpha (or HIF-1-α). HIF-1-α is responsible for the transcription of more than 100 genes, among them the genes encoding the angiogenic vascular endothelial growth factor (VEGF) and its kinase insert domain receptor (KDR). Tumors have a hypoxic environment and express HIF-1-α, which drives the vascularization of the tumor. Similarly, vascular lesions in the lungs from IPAH patients express HIF-1-α, VEGF and KDR, and while not tumors, are non-malignant growths. Thus, copper chelation would affect the transcription of HIF-1-α-dependent genes.

Second, copper plays a role in inflammation. It has long been appreciated that the lung vascular lesions in IPAH are infiltrated by inflammatory and immune cells (Tuder et al., Am J Pathol, 1994 February; 144(2): 275-85.) These cells secrete mediators of inflammation, so-called cytokines—specifically the interleukins IL-1 and IL-6 (Humbert et al., Am J Respir Crit Care Med., 1995 May; 151(5):1628-31). In several cell—and organ systems it has been shown that a specific copper chelator, TTM salt, reduces the secretion of cytokines, as the TTM salt has an anti-inflammatory action in addition to the anti-angiogenic action.

Figure 2:
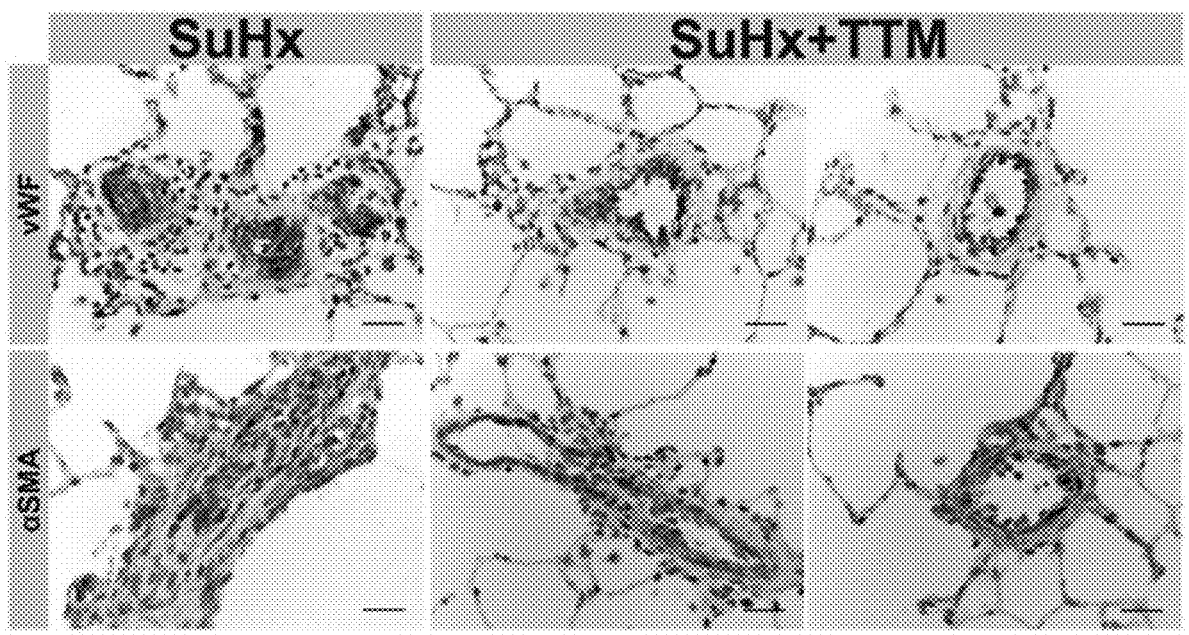
FIG. 2 shows the immunohistochemistry of rat lung vessels; two antibodies are used to identify endothelial cells and vascular smooth muscle cells; the comparison is made between Sugen/Hypoxia rats (SuHx) and TMM treated SuHx rats (SuHx+TTM) that had received 10 mg/kg of TTM every other day for 10 days via the intraperitoneal route (originally published in Bogaard et al., Am J Respir Crit Care Med., 2012; 46: 582-591, of which one of the present inventors, Norbert F. Voelkel, is a senior author); while the vessel lumina are occluded in the not-treated animals, they have been reopened under the influence of the TTM treatment (occlusive lesions staining partly positive for von Willebrand Factor (VWF), and partly positive for alpha smooth muscle (α-SMA))

Third, copper plays a role in the alteration of genes of the cytochrome P450. The lung and, in particular, the lung vascular endothelial cells (EC) are involved in drug metabolism and the handling of toxic substances. It is known that cigarette smoke toxins highly up-regulate the expression of specific drug metabolizing genes, the genes of the cytochrome P450 super-family. There are 56 known cytochrome P450 genes coding for 56 isozymes. These enzymes metabolize 75% of all drugs in use, including all of the vasodilator drugs conventionally used for PAH treatment. These enzymes also are involved in cell growth and differentiation, in cholesterol and estrogen metabolism and for many years a role of these enzymes in the pathogenesis of cancers has been examined (in particular prostate, breast and lung cancer) (Kwapiszewska G et al, Circulation Research, submitted 2019). Norbert F. Voelkel discovered that the drug Sugen 5416, a component of the Sugen-induced rat models of angio-obliterative PAH, induces some of these cytochrome P450 isozyme genes more than 200-fold (Al-Husseini et al, Pulm Circ. 2015 March; 5(1); 101-116). Copper, however, has been shown to cause liver and kidney disease attributed to alterations of cytochrome P450 enzyme activities, and copper chelation has been demonstrated to protect against liver and kidney disease by inhibiting cytochrome P450 gene alterations. Moreover, FIG. 2 demonstrates that copper chelation, specifically treatment with TTM established angio-obliterative PAH in the Sugen/hypoxia rat model reopens lung arterioles. Specifically, the vessel lumina are occluded in the not-treated animals (SuHx), whereas they have been reopened after the treated animals (SuHx+TTM) received 10 mg/kg TTM every other day for 10 days.

Fourth, copper plays a role in abnormal cancer-like cellular energy metabolism. It has been known for more than 70 years that cancer cells have a different energy metabolism, the cells are glycolytic (the so-called Warburg effect). A role for copper in intracellular ATP energy production has been established recently focusing on mitochondrial energy metabolism (Ishida S. et al Proc Natl Acad Sci USA. 2013 Nov. 26; 110(48): 19507-12). Copper chelation, however, is likely to normalize abnormal cancer-like-cellular energy metabolism that the present inventors believe is present in PAH. This has also been shown in adipocytes.

Fifth, copper plays a role in angiogenesis. As in cancer, the abnormal cellular phenotypes undergo several "switches" in the tissue. That is, there is the angiogenic switch, the cell metabolism, or glycolytic, switch, and an integrin switch, i.e. the abnormal cells express changed integrin receptor proteins or increase their numbers, thus changing the cell adhesion properties to the cellular matrix. Norbert F. Voelkel's studies using the Sugen/hypoxia rat model of angio-obliterative PAH provide the first example of normalization of one particular integrin receptor protein alpha v beta 3, which was over-expressed in the PAH lungs. From this result, Norbert F. Voelkel postulated that copper plays a role in the alterations of integrins and in the behavior of an extracellular adhesion molecule, called SPARC, which is also pro-angiogenic and has been investigated in various cancer tissues. Thus, a copper chelator would provide anti-angiogenic action.

One of the present inventors, Norbert F. Voelkel, determined that these five copper-dependent mechanisms involved in cell growth and differentiation, angiogenesis and inflammation are amenable to modification by treatment with a copper chelator comprising a TTM salt. Because of the potential for modifying any or each of these disease-contributing mechanisms the use of a copper chelator is proposed by Norbert F. Voelkel to treat severe forms of PAH and veno-occlusive disease. In more general terms, the basis for the use of TTM in the treatment of PAH is the quasi-malignant behavior, that is similar to cancer growths, of the abnormal lung vascular cells due to "abnormal copper handling".

In this context of this patent application, "abnormal copper handling" by the abnormally growing cells means and includes that there are potentially multiple and diverse reasons for the faulty handling of copper. There may be inherited or acquired mutations in the genes encoding copper transporters or copper binding proteins or mutations of one or several genes encoding cytochrome P450 enzymes causing abnormal copper handling and abnormal cellular metabolism.

The copper chelator comprises a salt of TTM, which is a highly effective copper-chelator for the purpose of the present invention. The salt may be according to formula I:

X(MoS$_4$)

X is $(2Li)^{+2}$, $(2K)^{+2}$, $(2Na)^{+2}$, $Mg^{+2}$, $Ca^{+2}$, or $\{[N^+(R^1)(R^2)(R^3)(R^4)][N^+(R^5)(R^6)(R^7)(R^8)]\}$;

$R^1$, $R^2$, $R^3$, $R^5$, $R^6$, and $R^7$ are independently H, or optionally substituted group selected from the group consisting of alkyl, alkenyl, alkynyl, aryl, heteroaryl, cycloalkyl, heterocycloalkyl, aralkyl, alkylaralkyl, heteroaralkyl, cycloalkylalkyl, and heterocycloalkyl alkyl; and $R^4$ and $R^8$ are absent or independently H, or optionally substituted group selected from the group consisting of alkyl, alkenyl, alkynyl, aryl, heteroalkyl, cycloalkyl, heterocycloalkyl, aralkyl, alkylaralkyl, heteroaralkyl, cycloalkyl alkyl, and heterocycloalkyl alkyl;

wherein when $R^4$ is absent, $R^1$ and $R^2$ together with N forms an optionally substituted 5- or 6-membered aromatic ring, wherein up to 2 carbon atoms in the ring may be replaced with a heteroatom selected from the group consisting of O, N, and S;

wherein then $R^8$ is absent, $R^5$ and $R^6$ together with N forms an optionally substituted 5- or 6-membered aromatic ring, wherein up to 2 carbon atoms in the ring may be replaced with a heteroatom selected from the group consisting of O, NH, and S;

wherein $R^1$ and $R^2$, $R^2$ and $R^3$, or $R^2$ and $R^4$, together with N optionally forms an optionally substituted cyclic structure;

wherein $R^5$ and $R^6$, $R^6$ and $R^7$, or $R^7$ and $R^8$, together with N optionally forms an optionally substituted cyclic structure;

wherein $R^4$ and $R^8$ may be joined by a covalent bond;

wherein $R^1$, $R^2$, $R^3$, $R^5$, $R^6$ and $R^7$ are each independently optionally substituted with one or more OH, oxo, alkyl, alkenyl, alkynyl, $NH_2$, $NHR^9$, $N(R^9)_2$, $-C=N(OH)$, or $OPO_3H_2$, wherein $R^9$ is each independently alkyl or $-C(=O)(O)$-alkyl;

wherein $R^4$ and $R^8$ are each independently optionally substituted with one or more OH, oxo, alkyl, alkenyl, alkynyl, $NH_2$, $NHR^9$, $N(R^9)_2$, $-C=N(OH)$, or $-^+(R^{10})_3$, wherein $R^{10}$ is each independently optionally substituted alkyl; and wherein one or more $-CH_2-$ groups in $R^1$, $R^2$, $R^3$, $R^4$, $R^5$, $R^6$, $R^7$ and $R^8$ may be replaced with a moiety selected from the group consisting of O, NH, S, S(O), and S(O)$_2$.

In an exemplary embodiment, X is $\{[N^+(R^1)(R^2)(R^3)(R^4)][N^+(R^5)(R^6)(R^7)(R^8)]\}$ according to formula (II):

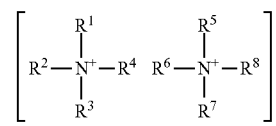

In one embodiment where X is $\{[N^+(R^1)(R^2)(R^3)(R^4)][N^+(R^5)(R^6)(R^7)(R^8)]\}$, $[N^+(R^1)(R^2)(R^3)(R^4)]$ and $[N^+(R^5)(R^6)(R^7)(R^8)]$ are the same or different.

In one embodiment where X is $\{[N^+(R^1)(R^2)(R^3)(R^4)][N^+(R^5)(R^6)(R^7)(R^8)]\}$, $R^1$, $R^2$, $R^3$, $R^5$, $R^6$, and $R^7$ are independently H or $C_1$-$C_{10}$ alkyl. In another embodiment where X is $\{[N^+(R^1)(R^2)(R^3)(R^4)][N^+(R^5)(R^6)(R^7)(R^8)]\}$, $R^1$, $R^2$, $R^3$, $R^5$, $R^6$, and $R^7$ are independently H, $C_1$-$C_3$ alkyl or $C_1$-$C_6$ alkyl. In a further embodiment where X is $\{[N^+(R^1)(R^2)(R^3)(R^4)][N^+(R^5)(R^6)(R^7)(R^8)]\}$, $R^4$ and $R^8$ are independently H or $C_1$-$C_6$ alkyl.

In one embodiment where X is $\{[N^+(R^1)(R^2)(R^3)(R^4)][N^+(R^5)(R^6)(R^7)(R^8)]\}$, $R^1$, $R^2$, $R^3$, $R^5$, $R^6$, and $R^7$ are independently H, methyl, ethyl or propyl. In a further embodiment where X is $\{[N^+(R^1)(R^2)(R^3)(R^4)][N^+(R^5)(R^6)(R^7)(R^8)]\}$, each of $R^1$, $R^2$, $R^3$, $R^4$, $R^5$, $R^6$, $R^7$ and $R^8$ is propyl, and the compound is tetrapropylammoniumtetrathimolybdate. In yet another embodiment where X is $\{[N^+(R^1)(R^2)(R^3)(R^4)][N^+(R^5)(R^6)(R^7)(R^8)]\}$, each of $R^2$, $R^3$, $R^4$, $R^5$, $R^6$, $R^7$ and $R^8$ is methyl, and the compound is tetramethylammoniumtetrathimolybdate. In even another embodiment where X is {[N⁺(R¹)(R²)(R³)(R⁴)][N⁺(R⁵)(R⁶)(R⁷)(R⁸)]}, each of R¹, R², R³, R⁴, R⁵, R⁶, R⁷ and R⁸ is ethyl, and the compound is tetraethylammoniumtetrathimolybdate.

In one embodiment where X is {[N⁺(R¹)(R²)(R³)(R⁴)][N⁺(R⁵)(R⁶)(R⁷)(R⁸)]}, R¹, R² and R³ are independently H, methyl, or ethyl and R⁴ is H or an optionally substituted alkyl, alkenyl, cycloalkyl alkyl, cycloalkyl, aryl, aralkyl, heterocycloalkyl, or heteroaryl. In another embodiment where X is {[N⁺(R¹)(R²)(R³)(R⁴)][N⁺(R⁵)(R⁶)(R⁷)(R⁸)]}, R⁵, R⁶, and R⁷ are independently H, methyl, or ethyl and R⁸ is H or an optionally substituted alkyl, alkenyl, cycloalkyl alkyl, cycloalkyl, aryl, aralkyl, heterocycloalkyl, or heteroaryl. In one embodiment where X is {[N⁺(R¹)(R²)(R³)(R⁴)][N⁺(R⁵)(R⁶)(R⁷)(R⁸)]}, the optional substituents for R⁴ and/or R⁸ are selected from the group consisting of alkyl, OH, NH₂, and oxo. In another embodiment where X is {[N⁺(R¹)(R²)(R³)(R⁴)][N⁺(R⁵)(R⁶)(R⁷)(R⁸)]}, one or more —CH₂— groups of R⁴ and/or R⁸ are replaced with a moiety selected from O, NH, S, S(O), and S(O)₂.

In an exemplary embodiment, the chelator compound is bis-choline tetrathiomolybdate.

In one embodiment, the copper chelator compound according to formula (I) is:

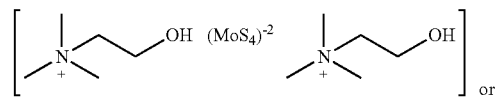

or

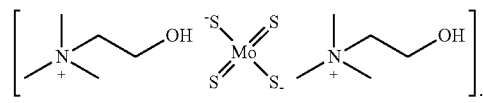

Table 1 provides non-limiting embodiments of where X is {[N⁺(R¹)(R²)(R³)(R⁴)][N⁺(R⁵)(R⁶)(R⁷)(R⁸)]}

TABLE 1

| | R¹ | R² | R³ | R⁴ | R⁵ | R⁶ | R⁷ | R⁸ |
|---|---|---|---|---|---|---|---|---|
| 1 | H | H | H | H | H | H | H | H |
| 2 | CH₃ | CH₃ | CH₃ | CH₃ | CH₃ | CH₃ | CH₃ | CH₃ |
| 3 | ethyl | ethyl | ethyl | ethyl | ethyl | ethyl | ethyl | ethyl |
| 4 | propyl | propyl | propyl | propyl | propyl | propyl | propyl | propyl |
| 5 | butyl | butyl | butyl | butyl | butyl | butyl | butyl | butyl |
| 6 | pentyl | pentyl | pentyl | pentyl | pentyl | pentyl | pentyl | pentyl |
| 7 | H | H | H | H | CH₃ | CH₃ | CH₃ | CH₃ |
| 8 | H | H | H | H | ethyl | ethyl | ethyl | ethyl |
| 9 | H | H | H | H | propyl | propyl | propyl | propyl |
| 10 | H | H | H | H | butyl | butyl | butyl | butyl |
| 11 | CH₃ | CH₃ | CH₃ | CH₃ | ethyl | ethyl | ethyl | ethyl |
| 12 | CH₃ | CH₃ | CH₃ | CH₃ | propyl | propyl | propyl | propyl |
| 13 | CH₃ | CH₃ | CH₃ | CH₂CH₂OH | CH₃ | CH₃ | CH₃ | CH₂CH₂OH |

In one embodiment where X is {[N⁺(R¹)(R²)(R³)(R⁴)][N⁺(R⁵)(R⁶)(R⁷)(R⁸)]}, R¹, R², R³, R⁵, R⁶, and R⁷ are independently methyl and R⁴ and R⁸ is each optionally substituted alkyl. In yet another embodiment where X is {[N⁺(R¹)(R²)(R³)(R⁴)][N⁺(R⁵)(R⁶)(R⁷)(R⁸)]}, each of R¹, R², R³, R⁵, R⁶, and R⁷ are independently methyl and R⁴ and R⁸ is each optionally substituted ethyl. In a further embodiment where X is {[N⁺(R¹)(R²)(R³)(R⁴)][N⁺(R⁵)(R⁶)(R⁷)(R⁸)]}, R¹, R², R³, R⁵, R⁶, and R⁷ are independently methyl and R⁴ and R⁸ is each substituted ethyl, wherein the substituent is a hydroxyl. In one embodiment where X is {[N⁺(R¹)(R²)(R³)(R⁴)][N⁺(R⁵)(R⁶)(R⁷)(R⁸)]}, each of R¹, R², R³, R⁵, and R⁷ are independently methyl and R⁴ and R⁸ is each —CH₂CH₂—OH.

In one embodiment where X is {[N⁺(R¹)(R²)(R³)(R⁴)][N⁺(R⁵)(R⁶)(R⁷)(R⁸)]}, R¹, R², R³, R⁵, R⁶, and R⁷ are independently methyl; R⁴ and R⁸ is each optionally substituted alkyl; and the compound is tetramethylammoniumtetrathimolybdate. In yet embodiment where X is {[N⁺(R¹)(R²)(R³)(R⁴)][N⁺(R⁵)(R⁶)(R⁷)(R⁸)]}, each of R¹, R², R³, R⁵, R⁶, and R⁷ are independently methyl; R⁴ and R⁸ is each optionally substituted ethyl; and the compound is tetramethylammoniumtetrathimolybdate. In a further embodiment where X is {[N⁺(R¹)(R²)(R³)(R⁴)][N⁺(R⁵)(R⁶)(R⁷)(R⁸)]}, R¹, R², R³, R⁵, R⁶, and R⁷ are independently methyl; R⁴ and R⁸ is each substituted ethyl, wherein the substituent is a hydroxyl; and the compound is tetramethylammoniumtetrathimolybdate. In one embodiment where X is {[N⁺(R¹)(R²)(R³)(R⁴)][N⁺(R⁵)(R⁶)(R⁷)(R⁸)]}, R¹, R², R³, R⁵, R⁶, and R⁷ are independently methyl; R⁴ and R⁸ is each —CH₂CH₂—OH; and the compound is tetramethylammoniumtetrathimolybdate.

In one embodiment where X is {[N⁺(R¹)(R²)(R³)(R⁴)][N⁺(R⁵)(R⁶)(R⁷)(R⁸)]}, each of [N⁺(R¹)(R²)(R³)(R⁴)] and [N⁺(R⁵)(R⁶)(R⁷)(R⁸)] is independently:

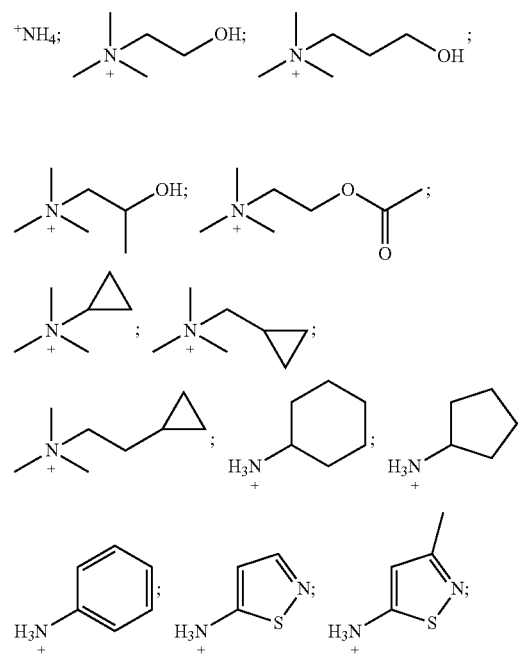

-continued

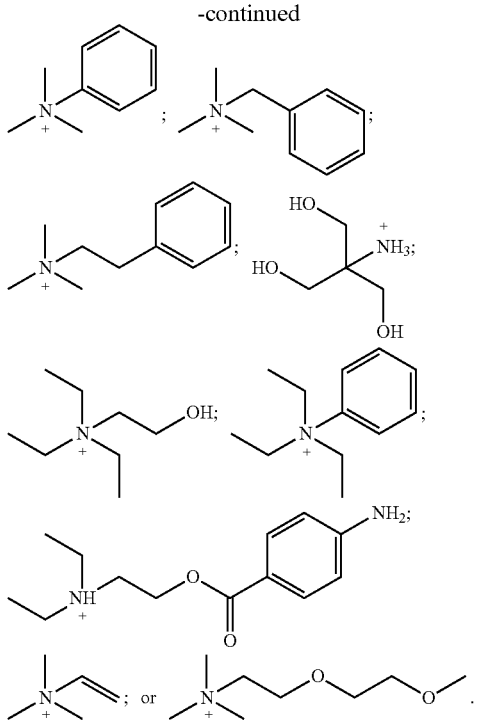

In one embodiment where X is $\{[N^+(R^1)(R^2)(R^3)(R^4)][N^+(R^5)(R^6)(R^7)(R^8)]\}$, at least one of $[N^+(R^1)(R^2)(R^3)(R^4)]$ and $[N^+(R^5)(R^6)(R^7)(R^8)]$ is:

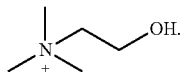

In another embodiment where X is $\{[N^+(R^1)(R^2)(R^3)(R^4)][N^+(R^5)(R^6)(R^7)(R^8)]\}$, both $[N^+(R^1)(R^2)(R^3)(R^4)]$ and $[N^+(R^5)(R^6)(R^7)(R^8)]$ are:

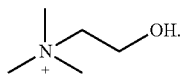

In one embodiment where X is $\{[N^+(R^1)(R^2)(R^3)(R^4)][N^+(R^5)(R^6)(R^7)(R^8)]\}$, $R^1$, $R^2$, $R^3$ and $R^4$ are each independently H or alkyl. In another embodiment, $R^5$, $R^6$, $R^7$ and $R^8$ are each independently H or alkyl.

In one embodiment where X is $\{[N^+(R^1)(R^2)(R^3)(R^4)][N^+(R^5)(R^6)(R^7)(R^8)]\}$, $R^4$ and $R^8$ are joined by a covalent bond. For example, if $R^4$ and $R^8$ are both methyl, when $R^4$ and $R^8$ are joined by a covalent bond, it can form an ethylene link between the two nitrogen atoms as illustrated below:

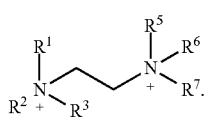

In one embodiment where X is $\{[N^+(R^1)(R^2)(R^3)(R^4)][N^+(R^5)(R^6)(R^7)(R^8)]\}$, $R^4$ and $R^8$ are both optionally substituted alkyl group joined by a covalent bond.

In one embodiment where X is $\{[N^+(R^1)(R^2)(R^3)(R^4)][N^+(R^5)(R^6)(R^7)(R^8)]\}$, $R^1$, $R^2$, $R^3$, $R^5$, $R^6$, and $R^7$ are independently H, methyl, ethyl or propyl and $R^4$ and $R^8$ are joined by a covalent bond. In one embodiment, $R^4$ and $R^8$ is each independently an optionally substituted alkyl group. In one embodiment, the optional substituents for $R^4$ and $R^8$ is $N^+(R^{10})_3$. In another embodiment, one or more —$CH_2$— groups of $R^4$ and $R^8$ are replaced with a moiety selected from the group consisting of O, NH, S, S(O), and $S(O)_2$.

In one embodiment where X is $\{[N^+(R^1)(R^2)(R^3)(R^4)][N^+(R^5)(R^6)(R^7)(R^8)]\}$, X is one of:

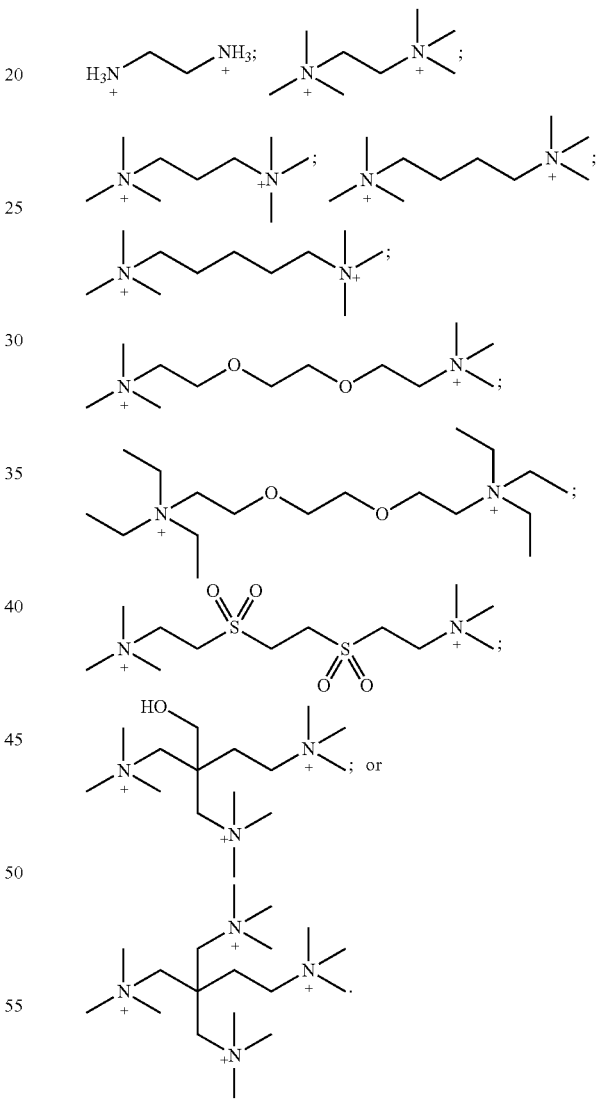

In one embodiment where X is $\{[N^+(R^1)(R^2)(R^3)(R^4)][N^+(R^5)(R^6)(R^7)(R^8)]\}$, $R^1$ and $R^2$ are each independently H, methyl, or ethyl and $R^3$ and $R^4$ are each independently an optionally substituted alkyl, aryl, or aralkyl group. In another embodiment where X is $\{[N^+(R^1)(R^2)(R^3)(R^4)][N^+(R^5)(R^6)(R^7)(R^8)]\}$, $R^5$ and $R^6$ are each independently H, methyl, ethyl or propyl and $R^7$ and $R^8$ are each independently an optionally substituted alkyl, aryl, or aralkyl group. In one embodiment, the optional substituents for $R^3$, $R^4$, $R^7$ and $R^8$ are OH.

In one embodiment where X is $\{[N^+(R^1)(R^2)(R^3)(R^4)][N^+(R^5)(R^6)(R^7)(R^8)]\}$, $[N^+(R^1)(R^2)(R^3)(R^4)]$ and/or $[N^+(R^5)(R^6)(R^7)(R^8)]$ is independently:

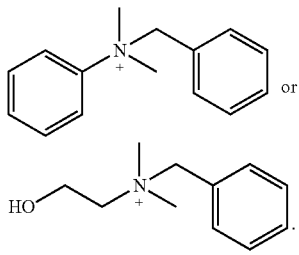

In one embodiment where X is $\{[N^+(R^1)(R^2)(R^3)(R^4)][N^+(R^5)(R^6)(R^7)(R^8)]\}$, $R^1$ and $R^4$ are each independently H, methyl, ethyl or propyl and $R^2$ and $R^3$ together with N may form an optionally substituted cyclic structure.

In another embodiment where X is $\{[N^+(R^1)(R^2)(R^3)(R^4)][N^+(R^5)(R^6)(R^7)(R^8)]\}$, $R^5$ and $R^8$ are each independently H, methyl, ethyl or propyl, and $R^6$ and $R^7$ together with N may form an optionally substituted cyclic structure. In one embodiment, one or more —$CH_2$— groups in $R^2$, $R^3$, $R^6$ and $R^7$ may be replaced with a moiety selected from the group consisting of O, NH, S, S(O), and S(O)$_2$.

In one embodiment where X is $\{[N^+(R^1)(R^2)(R^3)(R^4)][N^+(R^5)(R^6)(R^7)(R^8)]\}$, $[N^+(R^1)(R^2)(R^3)(R^4)]$ and/or $[N^+(R^5)(R^6)(R^7)(R^8)]$ is independently:

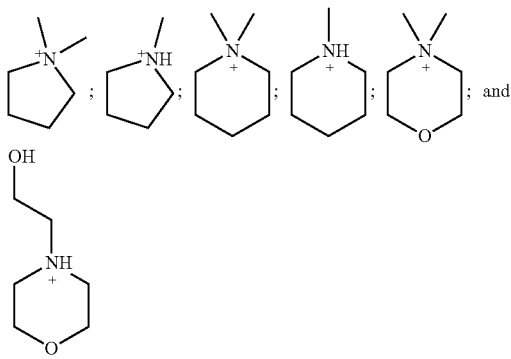

In one embodiment where X is $\{[N^+(R^1)(R^2)(R^3)(R^4)][N^+(R^5)(R^6)(R^7)(R^8)]\}$, $R^4$ and/or $R^8$ is absent and $R^1$ and $R^2$ and/or $R^5$ and $R^6$ together with N forms a optionally substituted 5- or 6-membered aromatic ring, wherein up to 2 carbon atoms in the ring may be replaced with a heteroatom selected from the group consisting of O, N, and S.

In one embodiment where X is $\{[N^+(R^1)(R^2)(R^3)(R^4)][N^+(R^5)(R^6)(R^7)(R^8)]\}$, $[N^+(R^1)(R^2)(R^3)(R^4)]$ and/or $[N^+(R^5)(R^6)(R^7)(R^8)]$ is independently:

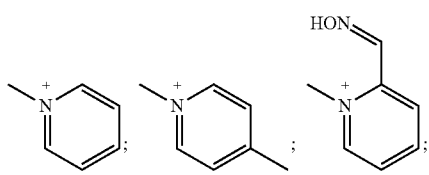

-continued

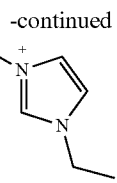

In one embodiment where X is $\{[N^+(R^1)(R^2)(R^3)(R^4)][N^+(R^5)(R^6)(R^7)(R^8)]\}$, wherein $R^1$, $R^2$, $R^3$, $R^4$, $R^5$, $R^6$, $R^7$ and $R^8$ are each H.

In an exemplary embodiment, the chelator compound is ammonium tetrathiomolybdate $[NH_4]_2MoS_4$ (ATTM). ATTM may be combined with other copper chelator compounds, such as ammonium trithiomolybdate $[NH_4]_2MoOS_3$.

In some exemplary embodiments, severe PAH in a patient is treated by administering a therapeutically effective amount of copper chelator comprising a TTM salt. In one exemplary embodiment, the copper chelator comprises ammonium tetrathiomolybdate $[NH_4]_2MoS_4$ (or ATTM), and in some exemplary embodiments the copper chelator may further comprise ammonium trithiomolybdate $[NH_4]_2MoOS_3$. The amount of a TTM salt delivered is individualized. In an exemplary embodiment, the therapeutically effective amount of the copper chelator delivers between 90 and 180 mg of ATTM/day. The amount of ATTM is adjusted according to the level of the ceruloplasmin in plasma. The effective copper chelation is achieved when the plasma ceruloplasmin level approaches 50% of the normal level; i.e. 15-17 mg/dl.

The copper chelator may be administered in a composition comprising pharmaceutically acceptable carriers and/or excipients. The compositions may be administered in an intravenous form or an oral form, such as a tablet, a microtablet, or a capsule. In some exemplary embodiments, the copper chelator may be in composition of an oral form with specific carriers and/or excipients that provide a delayed release of the copper chelator after passage through the stomach. Specifically, the carriers and/or excipients are selected to facilitate protection of the copper chelator against destruction by gastric acid and enabling optimal intestinal uptake and absorption. For example, the oral forms of the composition may include an enteric coating of the tablet or capsule or include a delayed release preparation.

At least one other active agent, or co-drug, is also contemplated in combination with the copper chelator comprising a TTM salt.

Figure 6:
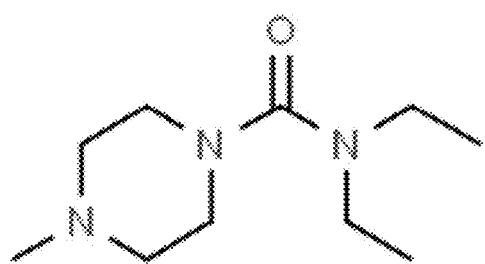
FIG. 6 illustrates the Structural formula of the 5-LO inhibitor DEC [Hetrazan] and known characteristics.
Figure 7:
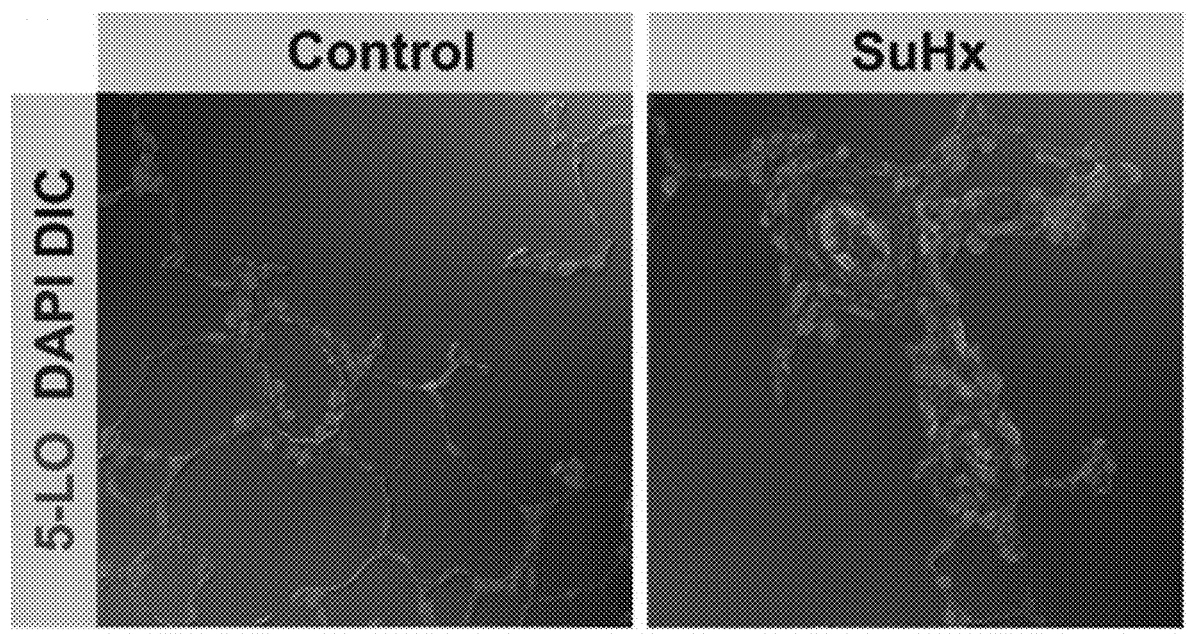
FIG. 7 compares immunofluorescence for representative tissue samples with the labeling of lumen-obliterating cells. Specifically, 5-LO protein expression in the lumen obliterating cells in a lung from a normal control rat is compared to the lung from a Sugen/Hypoxia rat (SuHx). Using differential interference contrast, it can be seen that the tissue 5-LO protein concentration was increased in the SuHx lungs, as analyzed by western blot (n=4-6), suggesting that the 5-LO is part of the disease process. (Al Husseini et al, 2015, PLoS One, March 18; 10(3))

For example, possible co-drugs include inhibitors of the 5-lipoxygenase enzyme (5-LO), which drives inflammation and likely controls cell growth, such as diethylcarbamazine (DEC), as described in FIG. 6, and zileuton. The 5-LO protein is expressed more in the pulmonary vessels of patients with severe PAH (as published in Wright et al, Am J Respir Crit Care Med, 1998 January; 157(1):219-29, of which Norbert F. Voelkel is a senior author). FIG. 7 shows that there is an increase in 5-LO protein expression in the SuHx rat lungs.

Figure 8:
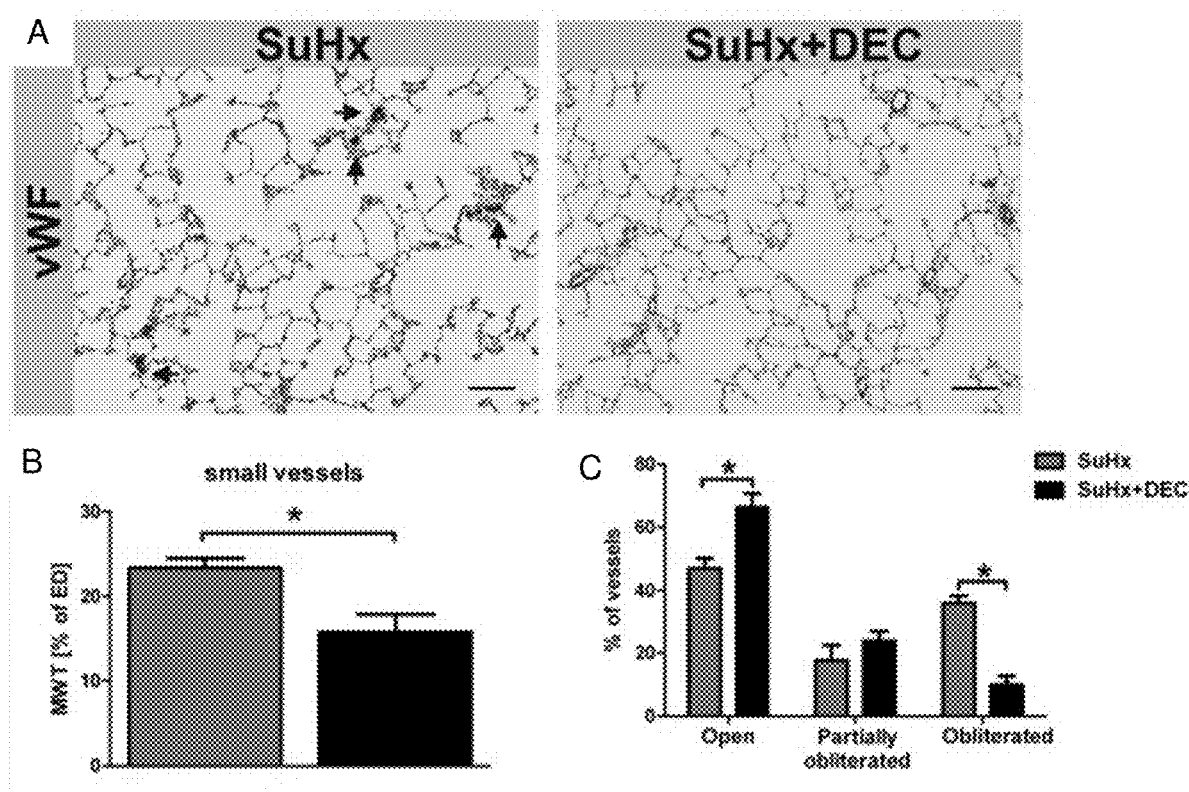
FIGS. 8A, B, and C demonstrate that diethylcarbamazine reopens occluded vessels in the Sugen/Hypoxia rat model (Al Husseini et al, 2015, PLoS One, March 18; 10(3)): A compares the von Willebrand factor (vWF) in Sugen/Hypoxia rats (SuHx) and in Sugen/Hypoxia rats (SuHx) treated with diethylcarbamazine (SuHx+DEC), scale bar 100 μm; B compares the molecular weights from small vessels in SuHx and SuHx+DEC, where ED=external diameter and MWT=media wall thickness, * designates a statistical significance level $p<0.05$ vs. control; C compares the percentage of open, partially obliterated and obliterated vessels for SuHx and SuHx+DEC, * designates a statistical significance level $p<0.05$ vs. control.

5-LO inhibitors have been shown to inhibit the development of PH in three different rodent models of PAH. Specifically, one of the present inventors, Norbert F. Voelkel, in particular demonstrated in a study from 2015 that DEC blunted the muscularization of pulmonary arterioles and reduced the number of fully obliterated lung vessels (Al Husseini et al, 2015, PLoS One, March 18; 10(3)) Specifically, in DEC treatment of Sugen/hypoxia rats, after the lung vascular disease had been established, reduced the degree of PAH, the number of obliterated arterioles and the degree of perivascular inflammation. The treatment lasted 3 weeks (21 days) with DEC being administered in an amount of 50 mg/kg daily treatment. The results are summarized in FIGS. 8A, B, and C. Norbert F. Voelkel concludes that the anti-inflammatory drug DEC affects developing PAH and is partially effective once angio-obliterative PAH has been established.

Thus, it is likely that the copper chelator comprising a TTM salt, and a 5-LO inhibitor work synergistically in PAH. While a TTM salt is expected to induce anoikis (inducing death of phenotypically abnormal pulmonary vascular cells), inhibition of 5-LO is expected to decrease inflammation and inhibit 5-LO-dependent cell growth. The 5-LO enzyme that is expressed in PAH lung vessel endothelial cells (but not in normal pulmonary vascular endothelial cells) acts in the context of pulmonary vascular disease as an activator of gene expression. 5-LO leads to the production of leukotriene C4, which is the first and well-established action of 5-LO, and leukotriene C4 increases pulmonary vasoconstriction by contracting smooth muscle cells in the bronchial airways and in the lung vessels. Thus, inhibiting 5-LO would also inhibit leukotriene C4 synthesis, which would remove a pulmonary vessel constricting substance. A second action is a non-enzymatic function of binding to the 5-LO activating protein [FLAP] on the envelope of the cell nucleus. Fitzpatrick and Lepley showed in 1998 that 5-LO co-precipitated with a subunit of the transcription factor NF-kappaB when they examined nuclear extracts. NF-kappaB controls the expression of genes encoding several LTB4 inflammatory mediators. Thus, 5-LO, by binding to NF-kappaB in the cell nucleus could activate transcription of a number of genes in control of cell growth and genes encoding inflammatory mediators such as IL-1beta and IL-6—and also VEGF. As a result of 5-LO inhibitor treatment, there could be a reduction in the vascular inflammation and perhaps stem cell reprogramming leading to halting of disease progression and assist disease reversal. LTB4 is another important chemotactic leukotriene that is a product of the enzyme leukotriene A4 hydrolase—which is downstream from 5-LO. LTB4 has recently been studied in the nude rat (athymic, no T lymphocytes) treated with the VEGF receptor blocker Sugen 5416. In this rat model it was demonstrated that LTB4 caused pulmonary endothelial cell apoptosis and that inhibition of LTB4 synthesis reversed angioproliferative PAH in this model (Tian W. et al Sci Transl Med. 2013 Aug. 28; 5(200):200ra117). Because effective inhibition of the 5-LO would also block LTB4 production, it is expected that 5-LO inhibitors in the treatment of PH would also target LTB4-dependent PH pathomechanisms.

In some exemplary embodiments, severe PAH in a patient may be treated with a therapeutically effective amount of a combination of copper chelator comprising a TTM salt and at least one 5-LO inhibitor. In particular, treatment of patient with severe forms of PAH, including IPAH and hereditary PAH, is possible with the administration of a therapeutically effective number of one of the 5-LO inhibitors diethylcarbamazine or zileuton in combination with a therapeutically effective amount of a copper chelator comprising a TTM salt.

Apigenin also affects, or specifically inhibits, NF-kappaB, and, thus, apigenin is also a suitable co-drug. Such an NF-kappaB inhibitor could be considered for the treatment of incident severe PAH—either alone or in combination with either a copper chelator comprising a TTM salt or the 5-LO inhibitors. Indeed, one inhibitor of NF-kappaB, pyrrolidine dithiocarbamate, has been shown to reverse established angio-obliterative PAH in the preclinical rat model of Sugen/hypoxia-induced PAH (Farkas D. et al AJRCMB, Vol. 15, No. 3, Sep. 1, 2014). Apigenin, in particular, has been shown to reduce inflammation. Thus, because 5-LO and the transcription factor NF-kappaB interact in the cell nucleus to initiate the expression of inflammatory and cell growth-promoting genes, then there would be an expected synergism in the drug action of a 5-LO inhibitor, such as zileuton or DEC, and apigenin. Likewise, the combination of apigenin with a copper chelator comprising a TTM salt is expected to provide the combined anti-inflammatory action of apigenin and the anti-angiogenic, anoikis-inducing action of the copper chelator comprising a TTM salt. Thus, some exemplary embodiments of concern are treating a patient suffering from PAH by administering a therapeutically effective amount of apigenin with a therapeutically effective amount of the copper chelator comprising a TTM salt.

Indole-3-carbinol (i3c) is another NF-kappaB inhibitor, and, thus, considered to be a suitable co-drug. I3c is a plant derived compound with a pleiotropic action profile, and it has been demonstrated that i3c has anti-inflammatory and anti-tumor growth activities. Specifically, i3c intervenes in signal transduction and controls cell growth by affecting several receptors and transcription factors. It inhibits the inflammation switchboard NF-kappaB and also is a ligand for the aryl hydrocarbon receptor (AhR), which is involved in drug metabolism and has been recently targeted for cancer therapy. Recently, it has been shown that i3c can upregulate the activity of the important tumor suppressor PTEN. Each of these pathways can explain the anti-inflammatory and anti-tumor effects of i3c. Levels of PTEN have been shown to be reduced in the lungs from pulmonary hypertensive animals and several experimental studies have shown that pulmonary vascular remodeling can be modulated in a PTEN-dependent manner. Thus, because inflammation and uncontrolled vascular cell growth are hallmarks of both PAH and cancer, treatment of PAH patients with i3c alone, or in combination with a copper chelator comprising a TTM salt, may reverse the pulmonary vascular lumen obliteration by inhibiting abnormal cell growth and inhibiting inflammation. Some exemplary embodiments of the present invention comprise treating a patient suffering from PAH by administering a therapeutically effective amount of i3c with a therapeutically effective amount of a copper chelator comprising a TTM salt.

Bufalin is another co-drug for consideration that may also have anti-inflammatory actions via inhibition of NF-kappaB and inhibition of the expression of the matrix metalloproteinases MMP2 and MMP9. Bufalin can also reduce the expression of the integrin alpha2/beta5. Significantly, bufalin is a multi-target anti-cancer agent, which appears to be promising for cancer treatment, and in several studies bufalin has been shown to inhibit the epithelial mesenchymal transition (EMT) in cancers—one of the hallmarks of cancer. This EMT inhibition occurs by downregulation of TGF beta receptor expression in lung cancer cells. This is considered relevant to PAH treatment because in PAH there is endothelial mesenchymal transition (EnMT) which is likewise TGF beta signaling dependent, bufalin is expected to inhibit EnMT in the sick lung vessels. In particular, the "plugs" occluding the vessel lumen in angioproliferative PAH consists of phenotypically altered cells (some have undergone EnMT), and very likely these cells rest on abnormal matrix proteins and these cells also very likely have undergone integrin switching. It is possible that a compound like bufalin may dissolve the cellular plug by interrupting TGF beta signaling and induce anoikis by altering abnormal integrins. Bufalin has not been tested in animal models of severe PAH and has not yet been clinically tested. However, bufalin's multi-modal action profile makes it a candidate as a co-drug with a copper chelator comprising a TTM salt in severe PAH, and, some exemplary embodiments of the present invention comprise treating a patient suffering from PAH by administering a therapeutically effective amount of bufalin with a therapeutically effective amount of a copper chelator comprising a TTM salt.

Another possible co-drug is methotrexate. Methotrexate (MTX) has been used for the treatment of breast cancer, leukemia, psoriasis and rheumatoid arthritis. MTX is of particular interest because it is an inhibitor of the enzyme dihydrofolate reductase and thereby inhibits DNA, RNA and protein synthesis, which is the desired action in cancer treatment at high MTX doses. Norbert Voelkel has prescribed MTX for one patient with pulmonary veno-occlusive disease, which is a rare form of severe PH. While Norbert Voelkel observed MTX treatment did not reverse the PH, MTX arrested the proliferative progression of this lethal disease and prolonged survival. By inhibiting DNA, RNA and protein synthesis, MTX is expected to play a supporting role to a copper chelator comprising a TTM salt, whereby MTX inhibits abnormal vascular cell growth while the copper chelator comprising a TTM salt promotes cell death of apoptosis-resistant vascular cells and reprograms stem cells.

In some exemplary embodiments, a therapeutically effective amount of a copper chelator comprising a TTM salt is administered with a therapeutically effective amount of MTX to treat patients with PAH. MTX has been a well-studied drug that has for decades been used for the treatment of breast cancer, leukemia, psoriasis and rheumatoid arthritis. The rationale for treating PAH patients with low-dose MTX is this: MTX is an inhibitor of the enzyme dihydrofolate reductase and thereby inhibits DNA, RNA and protein synthesis, which is (1) the desired action in cancer treatment that requires high MTX doses and (2) a desired action for deremodeling the growth of non-malignant cells within the PAH patients' lung's arteries when used in concert with TTM.

The anti-inflammatory and immune system affecting action of MTX is accomplished with low doses. MTX is known to inhibit T lymphocyte activation and decreases B lymphocyte numbers, it also inhibits the binding of IL-1 to cells. One patient with the uniformly lethal variant of severe PAH-pulmonary veno-occlusive disease (PVOD) has been treated by Norbert F. Voelkel with low dose MTX and progression of the PVOD was halted. PVOD is a fatal and extremely rare PH disorder. In the same patient, vasodilator treatment, which is the currently used treatment, resulted in lung edema. Vasodilator-induced lung edema precludes the use of vasodilator drugs in these patients.

The combination of MTX together with a copper chelator comprising a TTM salt can be considered as a treatment of patients with PAH, as an initial treatment, or as a treatment of PAH patients that do not respond to treatment by a copper chelator comprising a TTM salt alone.

Immune checkpoint inhibitors, e.g. inhibitors of CTLA-4, PD-1, and PDL-1 are also possible co-drugs. Severe PAH occurs in patients with autoimmune disorders like systemic sclerosis (scleroderma) and rheumatoid arthritis and in patients with immune insufficiency like AIDS. Moreover, and of importance, many patients with idiopathic forms of PAH also demonstrate markers of immune system abnormalities. For example, many of these patients have auto-antibodies (against endothelial cells and anti-nuclear antibodies) and one feature shared by patients with autoimmune disease-associated PAH and idiopathic PAH (IPAH) patients are regulatory T cell abnormalities. For this reason, the selection of inhibitors of CTLA-4, PD-1, and PDL-1 or immune checkpoint inhibitors are proposed. These agents developed by NECTAR has used IL-2 receptor-stimulating proteins that enlarge the CD 8+ lymphocyte pool (NKTR-214, NKTR 358, NKTR 262 and other T Cell enhancing therapies) may have a positive effect when used in concert with a copper chelator comprising a TTM salt. NKTR 214 is a CD122-preferential IL-2 pathway agonist, NKTR 358 is an IL-2 conjugate Treg stimulator that targets the interleukin (IL-2) receptor complex in the body in order to stimulate proliferation of powerful inhibitory immune cells known as regulatory T cells. NKTR-262, is a novel toll-like receptor (TLR) 7/8 agonist, is designed to induce the body's innate immune response to prime antigen-specific cytotoxic T cells to fight cancer. Thus, in some embodiments, treatment of a patient suffering from severe PAH is carried out by administering a therapeutically effective amount of a copper chelator comprising a TTM salt with a therapeutically effective amount of at least one co-drug known for immuno-modulation. Because of this overlap of autoimmune disease-associated forms of PAH with idiopathic pulmonary arterial hypertension, (IPAH, WHO Group 1) anti-inflammatory and immune-modulating strategies make sense.

In some exemplary embodiments, a therapeutically effective amount of a copper chelator comprising a TTM salt may be administered to a patient suffering from PAH in concert with a therapeutically effective amount of an immune checkpoint (CTLA-4, PD-1, PDL-1) inhibitors and agents developed by NECTAR that use IL-2 receptor stimulating proteins that enlarge the CD 8+ lymphocyte pool (e.g. NKTR-214 and others).

For example, in a rat model of severe and lethal PAH in athymic animals that do not have T-lymphocytes, PH can be prevented and reversed by transplanting Treg lymphocytes (Tamosiuniene et al, Circ Res, 2011, 11; 179, of which Norbert F. Voelkel is an author). Short of a Treg cell transplant the above stated immune checkpoint blockers and agents like NKTR 214 may be effective in patients with severe PAH. For this reason, an effective amount of a copper chelator comprising a copper chelator comprising a TTM salt in concert with an effect amount of, for example NKTR 214, may be more effective than treatment of PH with only a copper chelator comprising a TTM salt.

Other combinations of copper chelators comprising a TTM salt with effective amounts of immune checkpoint blockers inhibitors, e.g. PD-1 inhibitors or PDL-1 inhibitors would be also possible. The rationale for such a combination therapy using fundamentally mechanistically different agents in combination is that induction of lumen-obliterating lung cells by anoikis (due to the copper chelator comprising a TTM salt) and immune modulation accomplished by PD-1/PDL-1 or NKTR 214 may be complementary, and, thus, expected that more PAH patients will respond significantly to the treatment with the combined agents than with either the copper chelator comprising a TTM salt alone or NKTR 214 alone.

Rituximab is also a possible co-drug. Rituximab is a B-lymphocyte-depleting CD-20 antibody, and it is contemplated whether B lymphocyte depletion in PAH-associated with scleroderma will have an effect on pulmonary vascular remodeling. For example, a single immune system-modulating treatment strategy that has been studied by the present inventor's is treatment of scleroderma-associated PH patients with a single injection of a therapeutically effective amount of the B-lymphocyte-depleting CD-20 antibody, rituximab. Thus, an additional therapeutically effective amount of a copper chelator comprising a TTM salt can also be administered in concert.

Norbert F. Voelkel has already demonstrated that rats immunized with ovalbumin and treated with a single injection of the VEGF receptor blocker Sugen 5416, which develop severe angio-obliterative PAH, can be treated using a rituximab analog for elimination of B lymphocytes and the prevention of PAH development. In addition to B cell-directed strategies, because of known T lymphocyte abnormalities in patients with severe PAH, a rational approach can be directed towards immune modulation in PAH patients. A therapeutically effective amount of rituximab in a single injection and a therapeutically effective amount of a copper chelator comprising a TTM salt can be administered in concert to treat such PAH patients.

Co-drugs that are directed against integrins, i.e. antibodies against integrins, are also considered. Integrins are receptors involved in cell adhesion and cell signaling. Upon binding to the extracellular matrix, the integrins regulate cell survival proliferation, migration and cell phenotype transitions. Integrin signaling is dysregulated in cancers. Of interest, different integrins bind to growth factor receptors, e.g. alpha v/beta 3 binds to the VEGF receptor. Because the matrix protein composition of vascular smooth muscle cells in PH is altered, for example there is over-expression of tenascin which binds to alpha v/beta 3, and both chronic hypoxia and monocrotaline models of PAH also show an overexpression of alpha v and beta 3. In cancers there is an overexpression of alpha 2 and it is hypothesized that this overexpression of alpha v/beta 3 in part causes cancerous growths. It is expected that antibody treatment inactivates the signaling through these receptors and induce anoikis of the lumen-obliterating cells. Abnormal matrix proteins and bound to them integrin receptors form the "glue between the abnormal lumen-obliterating cells". As in cancer, integrin signaling may enhance the capacity of the phenotypically altered vascular cells in the PAH disease to resist the effects of therapy. Alpha v/beta 3 may support "stemness" of cells. Strategies directed towards integrins are likely to augment the effects of a copper chelator comprising a TTM salt as an anoikis-inducer and increase the number of patients responding to treatment by a copper chelator comprising a TTM salt. In Norbert F. Voelkel's study of severe PAH (Bogaard et al., Am J Respir Crit Care Med., 2012; 46: 582-591) it was found that the reopening of obliterated lung vessels by a copper chelator comprising a TTM salt was associated with reduced the expression of the alpha v/beta 3 integrin protein.

Thus, in some exemplary embodiment's treatment of PAH and severe PAH in a patient may be treated with a therapeutically effective amount of the copper chelator comprising a TTM salt and a therapeutically effective number of antibodies against integrins.

Focal adhesion kinase (FAK) inhibitors, such as disulfiram, fucoxanthinol, and nintedanib are also suitable co-drugs. FAK inhibitors can induce anoikis, and, thus, because the principle effect of the treatment with a copper chelator comprising a TTM salt is believed to be the induction of anoikis, their combination with a copper chelator comprising a TTM salt is expected to be beneficial. In at least one embodiment, an induction of anoikis in lung vessel cells is achieved by administering a therapeutically effective amount of a copper chelator comprising a TTM salt and at least one other anoikis-inducing agent such as baicalin, FAK inhibitors, including disulfiram, fucoxanthinol, and nintedanib, and antibodies against integrins. Lung vessel cells include those of patient's suffering from PH or PAH, and the induced anoikis treats the PH or PAH.

Other possible co-drugs include naturally occurring plant products, specifically baicalin, curcumin and quercetin, which are useful for the treatment of early diagnosed PAH. These compounds were identified as copper handling modifiers in a Chinese publication that analyzed studies where plant extracts in various combinations were used to treat patients with the copper storage Wilson disease (Xu M-B, Rong P-Q et al, Front in Pharmacol, 2019). The authors reference experimental data indicating that curcumin, baicalin and quercetin can alter intracellular copper handling. However, each of these compounds have been shown to possess other activities which are also relevant to treating PH or PAH.

Of these three compounds, baicalin has received the most attention in recent years. Baicalin is an extract from a Chinese herb that has been used to treat many diseases in China for centuries. In particular, there are four findings that are most relevant to treating PH or PAH. First, a high dosage of baicalin was found to inhibit angiogenesis through the induction of apoptosis. This relevant because severe PAH is a disease of misguided angiogenesis, and, thus, baicalin could inhibit angiogenesis in PAH. Second baicalin was found to alleviate silica-induced lung inflammation and fibrosis by inhibiting T-helper 17 cell (TH 17), or more broadly it was shown to stimulate Tregs and be an anti-inflammatory. This is relevant because baicalin could, thus, inhibit pulmonary vascular inflammatory cell infiltration. Third, baicalin was found to inhibit colon cancer by apoptosis and cellular senescence. This is relevant because MAPK/ERK pathways have also been implicated in PAH, and baicalin could induce apoptosis of the apoptosis-resistant lumen-filling cells in severe PAH. Fourth, baicalin was found to attenuate monocrotaline-induced pulmonary hypertension through the bone morphogenetic protein signaling pathway, having an anti-inflammatory effect. This is relevant because of the beneficial effect in this model of inflammation-triggered PH.

Furthermore, The American Journal of Respiratory and Critical Care Medicine in Dec. 1, 2018 published a study that was performed to determine whether targeting hypoxia-inducible factor-2alpha (HIF-2$\alpha$) with a HIF-2$\alpha$-selective inhibitor could reverse PAH and RHF in various rodent PAH models. The findings demonstrated that pharmacological inhibition of HIF-2$\alpha$ is a promising novel therapeutic strategy for the treatment of severe vascular remodeling and right heart failure in patients with PAH. HIF-1$\alpha$ & HIF-2$\alpha$ control the transcription of >100 genes, and both factors have been implicated to have important roles in cancer and PAH. The recently published results obtained in rat models of PAH demonstrate that pharmacological inhibition of HIF-2$\alpha$ may be a promising novel therapeutic strategy for the treatment of severe vascular remodeling and right heart failure in patients with PAH. Thus, both a copper chelator comprising a TTM salt and baicalin inhibit HIF-1$\alpha$, and a copper chelator comprising a TTM salt also inhibits HIF-2$\alpha$.

It is possible that adding baicalin to a dose of a copper chelator comprising a TTM salt may improve the cell death and assist in reversing PAH. Thus, in some exemplary embodiments a patient suffering from PAH can be treated by administering a therapeutically effective amount of the copper chelator comprising a TTM salt and a therapeutically effective amount of baicalin.

Curcumin is a diarylheptanoid extracted from turmeric, which has long been considered to have anticancer effects, and there is a voluminous literature describing the effects of curcumin in many models of cancer and inflammatory diseases. However, while the literature focuses on its antioxidant and anti-inflammatory properties, Curcumin has also been shown to induce the pulmonary anti-hypertensive Heme oxygenase 1 and has protective effects against lung injury via TGF beta 1 inhibition. It suppresses gastric carcinoma by inducing apoptosis of the tumor cells. Thus, curcumin may inhibit the inflammatory component of pulmonary vascular remodeling, and it is possible that curcumin could inhibit pulmonary vascular cell proliferation via inhibition of the signal transducer and activator of transcription 3 (STAT3) signaling pathway. Because inflammation is an important component of the angiopathy in severe PAH, curcumin may be a non-toxic partner with a copper chelator comprising a TTM salt in the treatment of severe PAH. Indeed, it has been shown that curcumin derivatives were mild phosphodiesterase V inhibitors (acting like a pulmonary vasodilator), and, it has been suggested that curcumin could be used to treat PAH. Thus, in some exemplary embodiments a patient suffering from PAH or severe PAH can be treated by administering a therapeutically effective amount of the copper chelator comprising a TTM salt and a therapeutically effective amount of curcumin.

Quercetin is a plant flavonoid contained in many plants and vegetables like broccoli and onions, and its antioxidant activities are well-documented. However, Quercetin has also been shown to inhibit VEGF expression and VEGF receptor 2 signaling, and, thus, it is anti-angiogenic. It has also been shown to inhibit glycolysis in breast cancer cells (one of the hallmarks of cancer), vascular remodeling in rodent models of PH, and endothelial-mesenchymal transformation (EnMT). Moreover, it has been shown that quercetin improves wound healing by modifying the integrin alpha v/beta 1. Thus, because of its anti-angiogenic and antioxidant action profile, quercetin may inhibit the angio-obliterative cell growth in PAH. Given the central problem of lumen obliteration in severe PAH and the importance of EnMT in severe PAH, quercetin is a good and non-toxic co-drug together with a copper chelator comprising a TTM salt. Thus, in some exemplary embodiments a patient suffering from severe PAH can be treated by administering a therapeutically effective amount of the copper chelator comprising a TTM salt and a therapeutically effective amount of quercetin.

The known and expected effects of the copper chelator comprising a TTM salt (listed as "TTM") and the above discussed other active agents, or co-drugs are summarized below in Table 2.

TABLE 2

| Drug Agent | Expected Effect On PAH | Expected Combined Effect with TTM |
| --- | --- | --- |
| TTM | Anti-angiogenesis Anti-inflammation Modification of stem cell behavior | |
| MTX | Anti-inflammation Inhibition of cell growth | TTM and MTX have different mechanisms of action but may act synergistically to inhibit abnormal cell growth. |
| 5-LO inhibitors, e.g. DEC and Zileuton. | Anti-inflammation Inhibition of pulmonary and vasoconstriction | TTM & 5-LO inhibition may be synergistic: TTM is anti-angiogenic and 5-LO inhibition decreases inflammation. |

TABLE 2-continued

| Drug Agent | Expected Effect On PAH | Expected Combined Effect with TTM |
| --- | --- | --- |
| Rituximab | Reduction of B lymphocytes Effect on immune system abnormalities | TTM & rituximab may be synergistic: anti-angiogenesis & immune response modulation. |
| Baicalin | Anti-inflammation | TTM & baicalin are both inducing anoikis—but by different molecular mechanisms. |
| FAK inhibitors, e.g. Disulfiram, Fucoxanthinol, and Nintedanib. | Reopening of occluded lung vessels | May be synergistic with TTM in their action of anoikis induction. |
| Immune checkpoint [CTLA-4, PD-1, PDL-1] inhibitors Immune modulation by agents developed by NEKTAR— NKTR 214 & NKTR 358 | Increase of T Cells Prevention of PAH growth | TTM is anti-angiogenic and immune checkpoint inhibitors may kill cells by an independent mechanism. |
| Inhibitors of NF-kappaB, such as Apigenin | Inhibition of NF-kappaB dependent gene transcription | TTM is anti-angiogenic and NF-kappaB inhibitors are anti-inflammatory |
| Bufalin | Reopening of occluded lung vessels | Mechanism of inducing death of abnormal cells likely different from that of TTM. |
| Quercetin | Decrease in inflammatory cells in the lung vascular lesions | Anti-inflammation synergism with TTM. |
| Curcumin | Decrease in the inflammatory cells in the lung vascular lesions and pulmonary vasodilation. Effect on copper handling in cell | Anti-inflammation synergism with TTM. |
| Antibodies against Integrins | Induction of anoikis of the lumen-obliterating cells | Mechanism of inducing anoikis may be different from that of TTM and there may synergism. |

In terms of administration, some exemplary embodiments concerning the administration of both the copper chelator comprising the TTM salt and the co-drug is in a single dose form or composition, and in other exemplary embodiments the copper chelator comprising a TTM salt and co-drugs are administered in separate compositions. In some exemplary embodiments, the TTM salt—with or without a co-drug—is administered 90 to 180 mg/day, which is adjusted to the target ceruloplasmin level of 50% of its normal value; for practical purposes this target is 15-17 mg/dl of plasma.

The compositions may comprise pharmaceutically acceptable carriers and/or excipients. The compositions may be in an intravenous form or an oral form, such as a tablet, a microtablet, or a capsule. In some exemplary embodiments, the copper chelator comprising a TTM salt may be in composition of an oral form, and the co-drug may be in composition of an intravenous form. For compositions comprising the copper chelator comprising a TTM salt, with or without the co-drugs, specific carriers and/or excipients may be added to provide a delayed release of the TTM salt after passage through the stomach. Specifically, the carriers and/or excipients are selected to facilitate protection of the TTM salt against destruction by gastric acid and enabling optimal intestinal uptake and absorption. For example, the oral forms of the composition may include an enteric coating of the tablet or capsule or include a delayed release preparation.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments may be made by those skilled in the art without departing from the scope of the invention as defined by the following claims.

What is claimed is:

1. A method of treating pulmonary arterial hypertension (PAH) in a patient in need thereof, comprising administering to the patient a therapeutically effective amount of a pharmaceutical composition comprising: a copper chelator comprising a tetrathiomolybdate salt; diethylcarbamazine (DEC); and a pharmaceutically acceptable carrier.

2. The method of claim 1, wherein the copper chelator comprises a tetrathiomolybdate salt according to:

$X(MoS_4)$, wherein:
X is $(2Li)^{+2}$, $(2K)^{+2}$, $(2Na)^{+2}$, $Mg^{+2}$, $Ca^{+2}$, or $\{[N^+(R^1)(R^2)(R^3)(R^4)][N^+(R^5)(R^6)(R^7)(R^8)]\}$, $R^1$, $R^2$, $R^3$, $R^5$, $R^6$, and $R^7$ are independently H, or optionally substituted group selected from the group consisting of alkyl, alkenyl, alkynyl, aryl, heteroaryl, cycloalkyl, heterocycloalkyl, aralkyl, alkylaralkyl, heteroaralkyl, cycloalkyl alkyl, and heterocycloalkyl alkyl; and $R^4$ and $R^8$ are absent or independently H, or optionally substituted group selected from the group consisting of alkyl, alkenyl, alkynyl, aryl, heteroaryl, cycloalkyl, heterocycloalkyl, aralkyl, alkylaralkyl, heteroaralkyl, cycloalkyl alkyl, and heterocycloalkyl alkyl.

3. The method of claim 1, wherein the copper chelator comprises $[NH_4]_2MoS_4$.

4. The method of claim 1, wherein the pharmaceutical composition is administered orally.

5. The method of claim 4, wherein the pharmaceutical composition is administered orally in a delayed release oral form preparation that releases the copper chelator comprising a tetrathiomolybdate salt and the DEC after the oral form passes the stomach.

6. The method of claim 1, wherein the pharmaceutical composition is administered intravenously.

7. The method of claim 1, wherein the pharmaceutical composition further comprises at least one of immune checkpoints inhibitors selected from the group consisting of inhibitors of cytotoxic T-lymphocyte-associated protein 4 (CTLA-4), programmed cell death protein 1 (PD-1) and programmed cell death ligand 1 (PDL-1); bufalin; antibodies against integrins; and a focal adhesion kinase inhibitors selected from the group consisting of disulfiram, fucoxanthinol, and nintedanib.

8. A pharmaceutical composition comprising:
a copper chelator comprising a tetrathiomolybdate salt; diethylcarbamazine (DEC); and
a pharmaceutically acceptable carrier.

9. The pharmaceutical composition of claim 8, wherein the copper chelator comprises a tetrathiomolybdate salt according to:

$X(MoS_4)$, wherein:
X is $(2Li)^{+2}$, $(2K)^{+2}$, $(2Na)^{+2}$, $Mg^{+2}$, $Ca^{+2}$, or $\{[N^+(R^1)(R^2)(R^3)(R^4)][N^+(R^5)(R^6)(R^7)(R^8)]\}$, $R^1$, $R^2$, $R^3$, $R^5$, $R^6$, and $R^7$ are independently H, or optionally substituted group selected from the group consisting of alkyl, alkenyl, alkynyl, aryl, heteroaryl, cycloalkyl, heterocycloalkyl, aralkyl, alkylaralkyl, heteroaralkyl, cycloalkyl alkyl, and heterocycloalkyl alkyl; and $R^4$ and $R^8$ are absent or independently H, or optionally substituted group selected from the group consisting of alkyl, alkenyl, alkynyl, aryl, heteroaryl, cycloalkyl, heterocycloalkyl, aralkyl, alkylaralkyl, heteroaralkyl, cycloalkyl alkyl, and heterocycloalkyl alkyl.

10. The pharmaceutical composition of claim 8, wherein the copper chelator comprises $[NH_4]_2MoS_4$.

11. The pharmaceutical composition of claim 8, wherein the composition is in an intravenous form or an oral form.

12. The pharmaceutical composition of claim 8, wherein the composition is in an oral form and is a delayed release preparation that releases the copper chelator comprising a tetrathiomolybdate salt and the DEC after the oral form passes the stomach.

13. The pharmaceutical composition of claim 8, further comprising at least one selected from the group consisting of: immune checkpoint inhibitors selected from the group consisting of inhibitors of cytotoxic T-lymphocyte-associated protein 4 (CTLA-4), programmed cell death protein 1 (PD-1), and programmed cell death ligand 1 (PDL-1); bufalin; antibodies against integrins; and a focal adhesion kinase inhibitor selected from the group consisting of disulfiram, fucoxanthinol, and nintedanib.

* * * * *